United States Patent
Furukawa et al.

(10) Patent No.: US 7,132,253 B2
(45) Date of Patent: Nov. 7, 2006

(54) MODIFIED SARCOSINE OXIDASES, MODIFIED SARCOSINE OXIDASE GENES, AND METHODS FOR PREPARING THE MODIFIED SARCOSINE OXIDASES

(75) Inventors: Keisuke Furukawa, Noda (JP); Naoki Kajiyama, Noda (JP)

(73) Assignee: Kikkoman Corporation, Noda (JP)

( * ) Notice: Subject to any disclaimer, the term of this patent is extended or adjusted under 35 U.S.C. 154(b) by 0 days.

(21) Appl. No.: 10/990,477

(22) Filed: Nov. 18, 2004

(65) Prior Publication Data
US 2005/0287624 A1  Dec. 29, 2005

(30) Foreign Application Priority Data
Nov. 18, 2003  (JP)  ............................. 2003-387975
Jun. 23, 2004  (JP)  ............................. 2004-184690

(51) Int. Cl.
*C12Q 1/26*  (2006.01)
*C12Q 1/34*  (2006.01)
*C12P 21/06*  (2006.01)
*C12N 9/06*  (2006.01)
*C07H 21/04*  (2006.01)
*C12N 15/00*  (2006.01)

(52) U.S. Cl. .................. 435/25; 435/18; 435/191; 435/320.1; 435/69.1; 435/325; 435/192; 536/23.2

(58) Field of Classification Search ................ 435/189, 435/18
See application file for complete search history.

(56) References Cited

U.S. PATENT DOCUMENTS

| 4,216,292 A | 8/1980 | Ikuta et al. |
| 5,024,945 A | 6/1991 | Mayr et al. |
| 2005/0026265 A1* | 2/2005 | Furukawa et al. ........... 435/191 |

FOREIGN PATENT DOCUMENTS

| JP | 54-52789 | 4/1979 |
| JP | 56-92790 | 7/1981 |
| JP | 60-43379 | 3/1985 |
| JP | 2-265478 | 10/1990 |
| JP | 5-115281 | 5/1993 |

OTHER PUBLICATIONS

Accession No.: AAQ43507, Derwent Genseq.*
Suzuki et al. Biosen. Bioelect. 2001, vol. 16, pp. 725-733.*
Masaru Suzuki, "Purification and Some Properties of Sarcosine Oxidase from Corynebacterium sp. U-96", J. Biochem., vol. 89, 1981, pp. 599-607.
U.S. Appl. No. 10/990,477, filed Nov. 18, 2004, Furukawa et al.
U.S. Appl. No. 10/829,427, filed Apr. 22, 2004, Furukawa et al.

* cited by examiner

*Primary Examiner*—Rebecca E. Prouty
*Assistant Examiner*—Mohammad Y. Meah
(74) *Attorney, Agent, or Firm*—Oblon, Spivak, McClelland, Maier & Neustadt, P.C.

(57) ABSTRACT

A modified sarcosine oxidase having a lowered activity for N-ethylglycine. Such a modified oxidase may have the following physicochemical properties:
(a) action: hydrolyzes 1 mol of sarcosine to produce 1 mol of glycine and 1 mol of formaldehyde;
(b) substrate specificity: reactivity for N-ethylglycine is 70% or less compared with that of an unmodified protein;
(c) optimal pH: around 8.0;
(d) stable pH range: between 6.5 and 11.0;
(e) optimal temperature: 55° C.;
(f) thermostability: 55° C. or less; and
(g) molecular weight: approximately 43,000 (SDS-PAGE).

Genes, vectors and host cells encoding or expressing modified sarcosine oxidases. The modified sarcosine oxidases of the present invention can be used as reagents for measuring creatinine or creatine. The reagents containing the modified sarcosine oxidases used therein are hardly affected by N-ethylglycine, enabling more precise measurement than ever before.

12 Claims, No Drawings

MODIFIED SARCOSINE OXIDASES, MODIFIED SARCOSINE OXIDASE GENES, AND METHODS FOR PREPARING THE MODIFIED SARCOSINE OXIDASES

BACKGROUND OF THE INVENTION

1. Field of the Invention

The present invention relates to modified sarcosine oxidases having decreased reactivity for N-ethylglycine compared with that of an unmodified enzyme, modified sarcosine oxidase genes, and methods for preparing the modified sarcosine oxidases. Sarcosine is also known as N-methylglycine an amino acid found in muscles and other tissues. N-methylglycine (sarcosine) is chemically similar to N-ethylglycine (a metabolic product of certain anesthetics). Decreasing the reactivity of sarcosine oxidases for N-ethylglycine is important for improving the sensitivity and specificity of assays measuring sarcosine (N-methylglycine), especially in biological samples where N-ethylglycine may be present. Sarcosine is measured in conventional assays for creatinine and creatine which are important clinical indicators.

2. Background Art

Sarcosine oxidases are enzymes with catalytic activity to hydrolyze sarcosines to produce glycine and formaldehyde, which can be used to measure the amount of creatinine in human serum or urine, or can be utilized as diagnostic agents for various diseases such as renal disease.

It has previously been known that sarcosine oxidases are produced by bacterial strains such as those of the *Corynebacterium* genus (e.g., see J. Biochem., 89, 599 (1981)), *Bacillus* genus (e.g., see JP Patent Publication (Unexamined Application) No. 54-52789), *Cylindrocarbons* genus (e.g., see JP Patent Publication (Unexamined Application) No. 56-92790), *Pseudomonas* genus (e.g., see JP Patent Publication (Unexamined Application) No. 60-43379), and *Arthrobacters* genus (e.g., see JP Patent Publication (Unexamined Application) No. 2-265478). The polynucleotide or protein sequences for the sarcosine oxidases described by these documents are hereby specifically incorporated by reference.

The inventors have isolated sarcosine oxidase genes from the *Bacillus* genus (e.g., see SEQ ID NO: 2 of JP Patent Publication (Unexamined Application) No. 5-115281) (SEQ ID NO: 2) and succeeded in causing the enzymes to be expressed in a large amount by genetic engineering techniques (e.g., see JP Patent Publication (Unexamined Application) No. 5-115281). The polynucleotide or protein sequences for sarcosine oxidases described by these documents are also specifically incorporated by reference.

While sarcosine oxidases act on sarcosines (N-methylglycines) sarcosine oxidases are also known to react to N-ethylglycine, which is a metabolic product of anesthetics such as lidocaine. Since reagents containing sarcosine oxidases used therein are affected by N-ethylglycine, it has been impossible to precisely measure creatinine or creatine using such reagents. For example, conventional sarcosine oxidases exhibit specificity and sensitivity problems for determining sarcosine levels in subjects receiving anesthetics which metabolize into N-ethylglycine, see e.g., Roberts et al., *Clinical Chemistry* 34: 2569–2572, 1988.

Sarcosine levels are enzymatically measured during conventional enzymatic assays of creatinine levels. The serum creatinine level is a conventional indicator of kidney function and a normal or usual value ranges from about 0.8 to 1.4 mg/dl. Conventional enzymatic assays for creatinine involve conversion of creatinine into creatine which is then converted into sarcosine and urea. Sarcosine oxidase subsequently converts sarcosine into glycine, formaldehyde and hydrogen peroxide. By determining the amount of sarcosine in a sample or by determining the reaction products of sarcosine after the action of sarcosine oxidase, the creatinine content in a biological sample may be determined.

Conventional assays for creatinine using sarcosine oxidase are well known and are also disclosed by U.S. Pat. Nos: 4,740,465, 4,845,029 and 4,950,609, which are incorporated by reference. Such assays are used to diagnose many conditions which are described by the *MedLine Plus Medical Encyclopedia*, "Creatinine-serum" (Feb. 11, 2004 update). For example, greater than normal levels may indicate acute tubular necrosis, dehydration, diabetic nephropathy, eclampsia (a condition of pregnancy that includes seizures), glomerulonephritis, muscular dystrophy, pre-eclampsia (pregnancy-induced hypertension), pyelonephritis, reduced renal blood flow (shock, congestive heart failure), renal failure, rhabdomyolysis or urinary tract obstruction. Lower than normal levels are associated with muscular dystrophy (late stage) and myasthenia gravis. Creatinine levels are also measured in conjunction with other diseases or disorders including acute nephritic syndrome Alport syndrome, atheroembolic renal disease, chronic renal failure, complicated UTI (pyelonephritis), Cushing's syndrome, dementia due to metabolic causes, dermatomyositis, digitalis toxicity, ectopic Cushing's syndrome, end-stage renal disease, epilepsy, generalized tonic-clonic seizure, Goodpasture's syndrome hemolytic-uremic syndrome (HUS), hepatorenal syndrome, IgM mesangial proliferative glomerulonephritis, interstitial nephritis, lupus nephritis, malignant hypertension (arteriolar nephrosclerosis), medullary cystic disease, membranoproliferative GN I, membranoproliferative GN II, Noninsulin-dependent diabetes mellitus (NIDDM), polymyositis (adult), prerenal azotemia, primary amyloid, rapidly progressive (crescentic) glomerulonephritis, secondary systemic amyloid, thrombotic thrombocytopenic purpura and Wilms' tumor.

SUMMARY OF THE INVENTION

In view of the above described problems with conventional sarcosine oxidases, the present inventors were determined to develop sarcosine oxidases having decreased reactivity for N-ethylglycine. The inventors have now found that it is possible to genetically modify sarcosine oxidase genes, such as those obtained from the genus *Bacillus,* to obtain a sarcosine oxidase with decreased reactivity for N-ethylglycine and thus possible to develop improved assays for sarcosine, such as superior creatinine assays for kidney function.

More specifically, as a result of genetically modifying sarcosine oxidase genes derived from the *Bacillus* genus shown in SEQ ID NO: 2 of JP Patent Publication (Unexamined Application) No. 5-115281 (SEQ ID NO: 2) the inventors have succeeded in obtaining sarcosine oxidases having decreased reactivity for N-ethylglycine.

While not being limited to the following aspects, the present invention provides:

(1) A modified sarcosine oxidase having reduced activity for N-ethylglycine. Such a modified sarcosine oxidase generally has one or more of the following physicochemical properties:

(a) action: hydrolyzes 1 mol of sarcosine to produce 1 mol of glycine and 1 mol of formaldehyde;

(b) substrate specificity: reactivity for N-ethylglycine is 70% or less compared with that of an unmodified protein;
(c) optimal pH: about 8.0;
(d) stable pH range: between about 6.5 and 11.0;
(e) optimal temperature: about 55° C.;
(f) thermostability: about 55° C. or less; and
(g) molecular weight: approximately 43,000 (SDS-PAGE).
(2) Specific modified sarcosine oxidases may characterized by the following (a), (b), or (c):
(a) a protein having an amino acid sequence represented by SEQ ID NO: 1;
(b) a protein having an amino acid sequence wherein one or some amino acid(s) are deleted from, substituted with, or added to the amino acid sequence represented by SEQ ID NO: 1, and having sarcosine oxidase activity characterized by decreased reactivity for N-ethylglycine compared with that of an unmodified protein; or
(c) a protein having an amino acid sequence showing 80%, 85%, 90%, 95%, 99% or more homology to the amino acid sequence of SEQ ID NO: 1 and having sarcosine oxidase activity characterized by decreased reactivity for N-ethylglycine compared with that of the corresponding unmodified protein.
(3) A modified sarcosine oxidase gene, encoding the following protein (a), (b), or (c):
(a) a protein having the amino acid sequence represented by SEQ ID NO: 1,
(b) a protein having an amino acid sequence wherein one or some amino acid(s) are deleted from, substituted with, or added to the amino acid sequence represented by SEQ ID NO: 1, and having sarcosine oxidase activity characterized by decreased reactivity for N-ethylglycine compared with that of an unmodified protein; or
(c) a protein having an amino acid sequence showing 80%, 85%, 90%, 95%, 99% or more homology or similarity to the amino acid sequence represented by SEQ ID NO: 1 and having sarcosine oxidase activity characterized by decreased reactivity for N-ethylglycine compared with that of an unmodified protein.
(4) A recombinant DNA, having the sarcosine oxidase gene according to (3) inserted in a vector DNA.
(5) A transformant or transductant, comprising the recombinant DNA according to (4).
(6) A method for preparing a modified sarcosine oxidase, comprising cultivating the transformant or transductant according to (5) in a medium and collecting sarcosine oxidases from the culture.
(7) A reagent or diagnostic kit for measuring sarcosine, creatine, or creatinine, or for evaluating kidney function, containing the modified sarcosine oxidase according to (1) or (2). The modified sarcosine oxidase of the present invention can be used as a reagent for measuring creatinine or creatine. The reagent containing the modified sarcosine oxidase used therein is significantly less affected by N-ethylglycine, enabling more precise measurement than ever before. Such a kit may comprise a sarcosine oxidase having low activity for N-ethylglycine, conventional reagents and buffers, indicators, standards or controls, containers or packages for the reagents or for all the kit ingredients, instructions for use for detecting levels of sarcosine, creatine or creatinine or for using the kit to diagnose diseases associated with abnormal levels of these compounds, and charts or tables for relating a sarcosine, creatine or creatine level to a particular disease state. Conventional diagnostic devices, assays, tests, test strips, kits, systems, or automated systems which use the sarcosine oxidases of the present invention are also contemplated.

This specification includes part of all of the contents as disclosed in the specifications of Japanese Patent Applications No. 2003-387975 and 2004-184690, which are bases of the priority claim of the present application and which are explicitly incorporated by reference

DETAILED DESCRIPTION OF THE PREFERRED EMBODIMENTS

The present invention will now be described in detail.

The sarcosine oxidases of the present invention can be obtained by modifying genes encoding sarcosine oxidases. Genes encoding sarcosine oxidases used for modification are not particularly limited. Examples of such genes include sarcosine oxidase genes derived from the *Bacillus* genus (described in JP Patent Publication (Unexamined Application) No. 5-115281), which is hereby incorporated by reference.

Any known methods may be used as a means of modifying the above genes. Examples of such methods include: a point mutagenesis method, for example, by bringing a sarcosine oxidase expression plasmid (pSOM1) comprising the above sarcosine oxidase gene derived from the *Bacillus* genus (described in JP Patent Publication (Unexamined Application) No. 5-115281) into contact with a chemical mutagen such as hydroxylamine or nitrous acid or by PCR random mutagenesis; a site-directed mutagenesis method, which is a known technology of site-directed substitution or deletion mutation using commercially available kits; a method of selectively cleaving this recombinant plasmid DNA and then removing or adding the selected oligonucleotide, followed by ligation of the plasmid; and an oligonucleotide mutagenesis method.

Method useful for producing and screening mutants or variants, such as mutants or variants of sarcosine oxidases, are well-known in the art and are also described by *Current Protocols in Molecular Biology* (1987–2004), vols. 1–4. Generally, a nucleic acid sequence encoding a variant will have 70%, 80%, 85%, 90%, 95% or 99% homology or similarity to an unmodified native sequence. Such similarity may be determined by an algorithm, such as those described by *Current Protocols in Molecular Biology*, vol. 4, chapter 19 (1987–2004) or by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482–489 (1981), to find the best segment of identity or similarity between two sequences. Gap performs global alignments: all of one sequence with all of another similar sequence using the method of Needleman and Wunsch, J. Mol. Biol. 48:443–453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

Alternatively, a mutant or variant polypeptide may be characterized by the ability of a polynucleotide sequence which encodes it, to hybridize to a polynucleotide encoding the unmodified native polypeptide under stringent conditions. Polynucleotides may be double or single stranded. When such hybridization is carried out solely with single-stranded nucleic acids it would occur between the coding strand for the unmodified native polypeptide and the complementary (non-coding) strand for the mutant or variant polypeptide, or vice versa. When two or more duplex nucleic acids are hybridized together, both the coding strands and their complements are present. Stringent hybridization conditions may comprise hybridization at 5×SSC at a temperature of about 50 to 68° C. for the hybridization reaction. Washing may be performed using 2×SSC and optionally followed by washing using 0.5×SSC at 50 to 68° C. For even higher stringency, the hybridization or washing temperature may be raised to 68° C. or washing may be performed in a salt solution of 0.1×SSC. Other conventional high stringency hybridization procedures and conditions may also be used as described by *Current Protocols in Molecular Biology,* (1987–2004), see e.g. Chapter 2, which is hereby incorporated by reference. An example of such a nucleic acid would be a polynucleotide which hybridizes to the nucleic acid sequence of SEQ ID NO: 1 under stringent conditions and which encodes a polypeptide having sarcosine oxidase activity and with a similar or lower activity for N-ethylglycine as the polypeptide encoded by SEQ ID NO: 1. Alternatively, such a polynucleotide may hybridize under stringent conditions to a polynucleotide encoding a known unmodified sarcosine oxidase, but encode a polypeptide having sarcosine oxidase activity but with a lower activity for N-ethylglycine than the unmodifed sarcosine oxidase.

Mutant or variant polypeptides, as well as fragments of such polypeptides, are characterized by their sarcosine oxidase activity. Mutant or variant polynucleotide sequences are characterized by their degree of similarity to a native sarcosine oxidase sequence as well as by their capacity to encode polypeptides having sarcosine oxidase activity with a reduced or decreased reactivity for N-ethylglycine, for example a reactivity which is at least 70% less than that of the corresponding unmodified sarcosine oxidase or is at least 70% less than that of the sarcosine oxidase encoded by pSOM1. Such mutant or variant polypeptides may be obtained by mutagenesis of bacterial sarcosine oxidase genes, for example, genes from *Bacillus*, or may be obtained by mutagenesis of polynucleotide sequences such as that of SEQ ID NO: 1 which already encodes a sarcosine oxidase with reduced reactivity for N-ethylglycine. For example, a variant polypeptide having a reduced reactivity for N-ethylglycine may be encoded by a polynucleotide having at least 90–95% similarity with SEQ ID NO: 1 or by a sequence which hybridizes to SEQ ID NO: 1 under stringent conditions. Alternatively, a variant polypeptide having sarcosine oxidase activity and a reduced reactivity for N-ethylglycine may be encoded by a polynucleotide having at least 90–95% similarity with a known polynucleotide sequence which encodes a sarcosine oxidase, or which hybridizes under stringent conditions to such a sequence. Vector DNAs used herein may be any DNAs such as plasmid DNAs and bacteriophage DNAs. Specific vectors and host cells suitable for cloning and expressing DNA are described by *Current Protocols in Molecular Biology* (1987–2004) which is hereby incorporated by reference.

Subsequently, the recombinant DNAs treated as described above are purified using a demineralized column such as QIAGEN (Funakoshi) to obtain various recombinant DNAs.

Using various recombinant DNAs thus obtained, for example, *E. coli* K12, preferably *E. coli* DH5α, *E. coli* JM109 (TOYOBO), or XL1-Blue (STRATAGENE™) can be transformed or transduced to obtain transformants or transductants comprising recombinant DNAs carrying sarcosine oxidase genes with various mutations introduced therein.

Next, the reactivity of the sarcosine oxidases for N-ethylglycine is assayed and then transformants or transductants having decreased reactivity for N-ethylglycine compared with that of the corresponding unmodified sarcosine oxidase are obtained. The transformants express sarcosine oxidases with less activity for N-ethylglycine than the unmodified sarcosine oxidase. Such a transformant may express a sarcosine oxidase with little or no activity for N-ethylglycine. Generally transformants expressing polypeptides having 10, 20, 25, 30, 40, 50, 60, 70, 80 or 90% of the activity for N-ethylglycine of that of the unmodified starting sarcosine oxidase are selected. That is, if the unmodified sarcosine oxidase has an activity of 100 for N-ethylglycine, then the modified sarcosine oxidase preferably has an activity of between 10–90. Also, transformants may be selected which express polypeptides having 10, 20, 25, 30, 40, 50, 60, 70, 80, or 90% of the activity for N-ethylglycine compared to the sarcosine oxidase expressed by pSOM1, or which have substantially the same reduced activity or even less activity for N-ethylglycine than the sarcosine oxidase expressed by SEQ ID NO: 1. Of course, such transformants must also express sarcosine oxidase activity, are preferably stable within a pH range of about 6.5 to 11.0 and are preferably thermostable at 55° C. or less.

Optionally, a transformant which expresses a modified sarcosine oxidase with lowered activity for N-ethylglycine may also be selected on the basis of the heat stability of the sarcosine oxidase it expresses. For example, a modified sarcosine oxidase may be further selected for its increased heat stability between 55° C. and 65° C., for its stability when exposed to buffers or surfactants used in assay procedures or for its stability over time when stored at 0° C. to 25° C. Criteria and methods for selecting a sarcosine oxidase based on its stability to buffers or surfactants are disclosed by U.S. Pat. No. 4,845,029 which is incorporated by reference. Criteria and methods for selecting a sarcosine oxidase for heat stability are disclosed by U.S. Pat. No. 4,740,465, which is hereby incorporated by reference.

The thus obtained transformants or transductants are cultivated in nutrient media so as to be able to cause them to produce large amounts of the modified sarcosine oxidases. As a cultivation medium, for example, a medium used herein contains 1 or more nitrogen sources of yeast extract, peptone, meat extract, corn steep liquor, soybean, wheat koji exudates, or the like appropriately supplemented with 1 or more inorganic salts of potassium dihydrogen phosphate, dipotassium hydrogen phosphate, magnesium sulfate, ferric chloride, ferric sulfate, manganese sulfate, or the like and further sugars, vitamins, or other substances as necessary.

In addition, it is appropriate to adjust the initial pH of the medium to between, for example, 7 and 9. It is also preferred to carry out cultivation at a temperature, for example, between 30° C. and 42° C. and preferably at around 37° C. for 6 to 24 hours by, for example, submerged cultivation with aeration and agitation, shaking cultivation, or stationary cultivation. After cultivation, ordinary means for collecting enzymes can be used to collect sarcosine oxidases from the cultures.

The cultivated microbial cells are separated from the cultures by, for example, a procedure such as filtration or centrifugation, and then washed. Sarcosine oxidases are preferably collected from these microbial cells. In this case, the microbial cells may be used as they are. Sarcosine oxidases are preferably collected from the microbial cells by methods for disrupting the microbial cells using various disruption means such as a sonic homogenizer, a French press, or a Dyna-Mill, methods for lysing the microbial cell walls using cell-wall-degrading enzymes such as lysozyme, methods for extracting enzymes from the microbial cells using surfactants such as Triton X-100, or the like.

To isolate sarcosine oxidases from the thus obtained crude enzyme solution, ordinary methods for purifying enzymes can be used. For example, it is preferred to perform an appropriate combination of ammonium sulfate precipitation, precipitation with organic solvents, ion exchange chromatography, gel filtration chromatography, adsorption chromatography, electrophoresis, and the like.

After isolation or purification of the modified sarcosine oxidases, they may be prepared in a suitable form for use in an assay. For example, they may be bound to a solid substrate, such as a column, bead or microtiter plate, or alternatively covalently bound to another molecule such as a polysaccharide for stability, such as the polysaccharides described by U.S. Pat. No. 4,950,609 which is incorporated by reference.

(Enzyme Activity)

The activity of the enzymes was measured under the following conditions. Enzyme activity capable of generating 1 micromol of urea per minute is defined as 1 unit.

(Preparation of Reagents)

The following solutions were prepared as reaction reagents.
1) 0.2 M sarcosine, 100 mM Tris-HCl, 2 mM KCl, 0.05% Triton-X100 (pH 7.7) or 10 mM N-ethylglycine, 100 mM Tris-HCl, 2 mM KCl, 0.05% Triton-X100 (pH 7.7)
2) 80 U/ml POD solution
3) 0.2% phenol solution
4) 0.2% 4-aminoantipyrine solution
5) 0.3% SDS solution
6) 20 mM Tris-HCl, 1 mM KCl, 0.2% BSA (pH 7.7) (enzyme diluent)

Next, each of the above solutions was mixed in the following amounts to prepare an activity measurement solution.
1) 5 ml
2) 1 ml
3) 2 ml
4) 1 ml Measurements were carried out as follows:
1) 0.95 ml of the activity measurement solution was preincubated at 37° C. for 5 minutes.
2) 0.05 ml of an enzyme solution (adjusted to between 0.04 U/ml and 0.16 U/ml with the enzyme diluent) was added and mixed.
3) Reaction was carried out at 37° C. for 10 minutes.
4) After 10-minute reaction, the above 0.3% SDS solution was mixed in.
5) After leaving the solution to stand at 25° C. for 10 minutes, absorbance at 495 nm was measured. (OD sample)

Blanks were measured by mixing the 0.3% SDS solution before mixing the enzyme solution. (OD blank)

The present invention will now further be specifically described by the following nonlimiting Examples.

EXAMPLE 1

E. coli JM109 (pSOM1) containing a recombinant plasmid DNA (pSOM1) (FERM BP-3604) was cultivated in an LB medium (DIFCO). After collecting the bacterial cells, the pSOM1 recombinant plasmid DNAs were extracted and purified from these cells using QIAGEN (QIAGEN). Approximately 100 µg of the recombinant plasmids were obtained.

Using plasmids obtained, error-prone PCR was performed with N-terminal and C-terminal primers (SEQ ID NOS: 4 and 5). In particular, Ex-taq (TAKARA SHUZO) was used with these primers under a manganese concentration of 0.075 mM, and then a PCR amplification reaction was carried out for pSOM1.

After the completion of reaction, amplified fragments of sarcosine oxidase genes with various mutations introduced therein were treated with restriction enzymes BamHI and SpeI, before being ligated into BamHI- and SpeI-digests of unmutated pSOM1 recombinant plasmid DNAs using T4 ligase (Boehringer). After the completion of ligation, the reaction solution was subjected to transformation with competent Hi E. coli JM109 (TOYOBO), and then transformant colonies were obtained.

Subsequently, the thus obtained colonies were cultivated in 2 ml of a TY medium (containing 25 µg/ml kanamycin and 1 mM IPTG). After 18 to 24 hours of cultivation at 37° C., the bacterial cells were collected by centrifugation. Substitution with 20 mM Tris-HCl (pH 8.0) and 1 mM KCl (pH 7.7), sonication, and then centrifugation (12,000 r.p.m. and 3 minutes) were carried out.

The activity of the thus obtained supernatant was measured using sarcosine and N-ethylglycine as substrates. Enzymes having activity for sarcosine equivalent to that of the enzymes before mutation, but having decreased activity for N-ethylglycine compared therewith, were screened for.

Plasmids were isolated from strains producing the above enzymes and denoted "pSOM5." The plasmid pSOM5 was deposited with the International Patent Organism Depositary, the National Institute of Advanced Industrial Science and Technology (Tsukuba Central 6, 1-1-1 Higashi, Tsukuba, Ibaraki, Japan), under FERM BP-10025 (transferred from FERM P-19587). The base sequence of the sarcosine oxidase encoded by this plasmid was determined using the CEQ 2000 DNA Sequencing System (Beckman Coulter), revealing that in the sarcosine oxidase of the present invention tyrosine at amino acid 269 had been substituted with histidine (SEQ ID NO: 1).

EXAMPLE 2

E. coli JM109 (pSOM5) comprising the modified sarcosine oxidase genes obtained as described above was cultivated with shaking in 100 ml of a TY medium (1% bacto-tryptone, 0.5% bacto-yeast extract, and 0.5% NaCl (pH 7.5)) containing 25 µg/ml kanamycin at 37° C. for 16 hours. Subsequently, 10 ml of the culture was inoculated to 1 L of a TY medium that had been prepared similarly (except for containing 1 mM IPTG). After inoculation, it was cultivated at 120 r.p.m. and 37° C. for approximately 20 hours.

Step 1 (Preparation of Crude Enzyme Solution)

After the completion of cultivation, bacterial cells were collected by centrifuging 1 L of a cultivation solution, and the bacterial cells were suspended in 50 ml of a solution (20 mM Tris-HCl and 50 mM EDTA (pH 8.0)).

The thus obtained cell suspension was subjected to sonication, so that the bacterial cells were disrupted and a crude enzyme solution was obtained.

Step 2 (Ammonium Sulfate Precipitation)

Ammonium sulfate precipitation was performed by adding 20% ammonium sulfate to 50 ml of the crude enzyme solution obtained as described above.

Following ammonium sulfate precipitation, the precipitate was dissolved in a buffer comprising 50 mM KCl, 20 mM Tris-HCl, and 2 mM EDTA.

Step 3 (DEAE-TOYOPEARL Ion Exchange Chromatography)

The above crude enzyme solution was adsorbed to a column packed with 300 ml of DEAE-TOYOPEARL (TOSOH), washed with 600 ml of a solution (100 mM KCl, 20 mM Tris-HCl, and 2 mM EDTA (pH 8.0)), and then eluted with a solution (150 mM KCl, 20 mM Tris-HCl, and 2 mM EDTA (pH 8.0)). When the elution was completed, fractions with high purities were collected, concentrated, and then dialyzed against a 50 mM phosphate buffer containing 150 mM KCl and 2 mM EDTA.

Step 4 (Sephadex G-75 Gel Filtration)

A column packed with 200 ml of Sephadex G-75 (Pharmacia) bufferized with a 50 mM phosphate buffer containing 150 mM KCl and 2 mM EDTA was charged with 15 ml of the enzyme solution obtained in Step 3 to perform gel filtration. The activity of the purified enzyme obtained at around OD 280 nm was approximately 27 U.

EXAMPLE 3

The reactivity for N-ethylglycine of the modified sarcosine oxidase purified by the above method was compared with that of an unmodified sarcosine oxidase using unified sarcosine activity of 1.0 U/ml.

When the activity of the unmodified sarcosine oxidase for N-ethylglycine was determined to be 100%, activity for N-ethylglycine of the modified sarcosine oxidase (Y269H) was found to be 66.6%.

As described above, decreased reactivity for N-ethylglycine of the obtained modified sarcosine oxidase was shown.

Furthermore, the physicochemical properties of the modified sarcosine oxidase were as shown below:

Optimal pH: around 8.0,

Stable pH range: between 6.5 and 11.0,

Optimal Temperature: 55° C.,

Thermostability: 55° C. or less (pH 7.5 and 10 minutes),

Molecular weight: approximately 43,000 (SDS-PAGE).

Modifications and Other Embodiments

Various modifications and variations of the described sarcosine oxidases, genes encoding sarcosine oxidases, methods of their production or use as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the biological, biochemical, molecular biological, chemical, enzymological, medical, pharmaceutical arts or related fields are intended to be within the scope of the following claims.

Incorporation by Reference

Each document, patent, patent application or patent publication cited by or referred to in this disclosure is incorporated by reference in its entirety. However, no admission is made that any such reference constitutes prior art and the right to challenge the accuracy and pertinency of the cited documents is reserved. Specifically, priority applications JP 2003-387975, filed Nov. 18, 2003 and JP 2004-184690, filed Jun. 23, 2004, are hereby incorporated by reference.

What is claimed is:

1. A modified sarcosine oxidase, which comprises an amino acid sequence at least 95% homologous to SEQ ID NO: 1, wherein position 269 has histidine (His) and which:
   (a) hydrolyzes 1 mol of sarcosine to produce 1 mol of glycine and 1 mol of formaldehyde; and
   (b) has a substrate specificity characterized by a reactivity for N-ethylglycine which is 70% or less compared with that of the unmodified sarcosine oxidase encoded by SEQ ID NO: 2.

2. A modified sarcosine oxidase which comprises the amino acid sequence of SEQ ID NO: 1.

3. A kit comprising the modified sarcosing oxidase of claim 1 and instructions for its use in determining the amount of creatinine, creatine, or sarcosine in a sample.

4. A kit comprising the modified sarcosing oxidase of claim 2 and instructions for its use in determining the amount of creatinine, creatine, or sarcosine in a sample.

5. A reagent for measuring creatinine or creatine, containing the modified sarcosine oxidase according to claim 1.

6. A reagent for measuring creatinine or creatine, containing the modified sarcosine oxidase according to claim 2.

7. The modified sarcosine oxidase of claim 1, which is at least 99% homologous to SEQ ID NO: 1.

8. The modified sarcosine oxidase of claim 1, which has optimal enzymatic activity at a pH of about 8.0.

9. The modified sarcosine oxidase of claim 1, which is stable at a pH ranging from 6.5 to 11.0.

10. The modified sarcosine oxidase of claim 1, which has optimal enzymatic activity at a temperature of about 55° C.

11. The modified sarcosine oxidase of claim 1, which is thermostable at a temperature of 55° C. or less.

12. The modified sarcosine oxidase of claim 1, which has a molecular weight of approximately 43,000 Da as determined by SDS-PAGE.

* * * * *

SEQUENCE LISTING

<160> NUMBER OF SEQ ID NOS: 6

<210> SEQ ID NO 1
<211> LENGTH: 1164
<212> TYPE: DNA
<213> ORGANISM: Artificial Sequence
<220> FEATURE:
<223> OTHER INFORMATION: Modified sarcosine oxidase polynucleotide
      sequence
<220> FEATURE:
<221> NAME/KEY: CDS
<222> LOCATION: (1)..(1164)

<400> SEQUENCE: 1

```
atg agt aca cat ttt gat gtg att gtt gtt gga gca gga tca atg gga        48
Met Ser Thr His Phe Asp Val Ile Val Val Gly Ala Gly Ser Met Gly
1               5                   10                  15 atg gct gca ggg tac tat tta gca aaa caa gga gtc aaa aca tta ttg        96
Met Ala Ala Gly Tyr Tyr Leu Ala Lys Gln Gly Val Lys Thr Leu Leu
            20                  25                  30
```

```
                                                           -continued gtg gca ttc gat ccg ccg cat aca gaa gga agc cat cac ggt gat          144
Val Asp Ala Phe Asp Pro Pro His Thr Glu Gly Ser His His Gly Asp
        35                  40                  45 act cgc att atc cgc cat gct tac ggt gaa gga aga gaa tat gtt cca      192
Thr Arg Ile Ile Arg His Ala Tyr Gly Glu Gly Arg Glu Tyr Val Pro
    50                  55                  60 ttt gca cta aga gca caa gaa tta tgg tat gaa ctt gaa aat gaa aca      240
Phe Ala Leu Arg Ala Gln Glu Leu Trp Tyr Glu Leu Glu Asn Glu Thr
65                  70                  75                  80 cac aat aag att ttt aca aaa aca ggc gtt cta gtt ttt ggt ccg aaa      288
His Asn Lys Ile Phe Thr Lys Thr Gly Val Leu Val Phe Gly Pro Lys
                85                  90                  95 ggt gaa tcc gat ttc gtt gcc gaa aca atg gag gca gct gca gaa cat      336
Gly Glu Ser Asp Phe Val Ala Glu Thr Met Glu Ala Ala Ala Glu His
            100                 105                 110 tca ttg atc gtg gat tta ctt gag ggt gat gaa atc aat acg cgc tgg      384
Ser Leu Ile Val Asp Leu Leu Glu Gly Asp Glu Ile Asn Thr Arg Trp
        115                 120                 125 ccc ggc ata acg gtt cct gaa aac tat aat gca att ttt gaa cca aat      432
Pro Gly Ile Thr Val Pro Glu Asn Tyr Asn Ala Ile Phe Glu Pro Asn
    130                 135                 140 tca ggc gta ttg ttc agt gag aat tgt att cgt tca tac cgt gag ctg      480
Ser Gly Val Leu Phe Ser Glu Asn Cys Ile Arg Ser Tyr Arg Glu Leu
145                 150                 155                 160 gct gta gca aaa gga gca aaa att tta aca tat act cgt gtt gag gat      528
Ala Val Ala Lys Gly Ala Lys Ile Leu Thr Tyr Thr Arg Val Glu Asp
                165                 170                 175 ttt gaa gtt tct caa gac caa gtt aaa atc caa acg gca aat gga tcg      576
Phe Glu Val Ser Gln Asp Gln Val Lys Ile Gln Thr Ala Asn Gly Ser
            180                 185                 190 tac aca gct gat aaa tta atc gta agt atg ggt gct tgg aat agt aaa      624
Tyr Thr Ala Asp Lys Leu Ile Val Ser Met Gly Ala Trp Asn Ser Lys
        195                 200                 205 cta ctt tct aaa tta aat ctt gac atc cca tta cag cca tac cgc caa      672
Leu Leu Ser Lys Leu Asn Leu Asp Ile Pro Leu Gln Pro Tyr Arg Gln
    210                 215                 220 gtt gta gga ttt ttt gat tct aat gaa gca aag tac agc aat gat gtg      720
Val Val Gly Phe Phe Asp Ser Asn Glu Ala Lys Tyr Ser Asn Asp Val
225                 230                 235                 240 gat tat cca gca ttc atg gta gaa gta cca aaa ggt att tat tac gga      768
Asp Tyr Pro Ala Phe Met Val Glu Val Pro Lys Gly Ile Tyr Tyr Gly
                245                 250                 255 ttc cca agc ttc ggt ggc tgc ggt ttg aaa ata ggg tat cat acg tat      816
Phe Pro Ser Phe Gly Gly Cys Gly Leu Lys Ile Gly Tyr His Thr Tyr
            260                 265                 270 ggt caa caa atc gac cct gat acg att aac cgt gaa ttt ggt gct tat      864
Gly Gln Gln Ile Asp Pro Asp Thr Ile Asn Arg Glu Phe Gly Ala Tyr
        275                 280                 285 caa gag gat gaa agt aat ctt cgc gat ttc ttg gaa aaa tat atg cca      912
Gln Glu Asp Glu Ser Asn Leu Arg Asp Phe Leu Glu Lys Tyr Met Pro
    290                 295                 300 gaa gca aat ggc gag tta aaa cga ggc gca gct tgt atg tac acg aaa      960
Glu Ala Asn Gly Glu Leu Lys Arg Gly Ala Ala Cys Met Tyr Thr Lys
305                 310                 315                 320 aca cca gat gaa cat ttc gtg att gat act cat cca gaa cat tcc aat     1008
Thr Pro Asp Glu His Phe Val Ile Asp Thr His Pro Glu His Ser Asn
                325                 330                 335 gtt ttc gta gca gct ggt ttc tct gga cac ggc ttt aaa ttt tca agt     1056
Val Phe Val Ala Ala Gly Phe Ser Gly His Gly Phe Lys Phe Ser Ser
            340                 345                 350
```

```
gta gtc ggt gaa gtg tta agt caa tta gcg aca aca ggt aaa aca gaa    1104
Val Val Gly Glu Val Leu Ser Gln Leu Ala Thr Thr Gly Lys Thr Glu
        355                 360                 365 cat gat att tca att ttc tca ata aat cgt cct gct tta aaa cag aaa    1152
His Asp Ile Ser Ile Phe Ser Ile Asn Arg Pro Ala Leu Lys Gln Lys
    370                 375                 380 aca acg att taa                                                    1164
Thr Thr Ile
385

<210> SEQ ID NO 2
<211> LENGTH: 387
<212> TYPE: PRT
<213> ORGANISM: Artificial Sequence
<220> FEATURE:
<223> OTHER INFORMATION: Synthetic Construct

<400> SEQUENCE: 2

Met Ser Thr His Phe Asp Val Ile Val Val Gly Ala Gly Ser Met Gly
1               5                   10                  15

Met Ala Ala Gly Tyr Tyr Leu Ala Lys Gln Gly Val Lys Thr Leu Leu
            20                  25                  30

Val Asp Ala Phe Asp Pro Pro His Thr Glu Gly Ser His His Gly Asp
        35                  40                  45

Thr Arg Ile Ile Arg His Ala Tyr Gly Glu Gly Arg Glu Tyr Val Pro
    50                  55                  60

Phe Ala Leu Arg Ala Gln Glu Leu Trp Tyr Glu Leu Glu Asn Glu Thr
65                  70                  75                  80

His Asn Lys Ile Phe Thr Lys Thr Gly Val Leu Val Phe Gly Pro Lys
                85                  90                  95

Gly Glu Ser Asp Phe Val Ala Glu Thr Met Glu Ala Ala Glu His
            100                 105                 110

Ser Leu Ile Val Asp Leu Leu Glu Gly Asp Glu Ile Asn Thr Arg Trp
        115                 120                 125

Pro Gly Ile Thr Val Pro Glu Asn Tyr Asn Ala Ile Phe Glu Pro Asn
    130                 135                 140

Ser Gly Val Leu Phe Ser Glu Asn Cys Ile Arg Ser Tyr Arg Glu Leu
145                 150                 155                 160

Ala Val Ala Lys Gly Ala Lys Ile Leu Thr Tyr Thr Arg Val Glu Asp
                165                 170                 175

Phe Glu Val Ser Gln Asp Gln Val Lys Ile Gln Thr Ala Asn Gly Ser
            180                 185                 190

Tyr Thr Ala Asp Lys Leu Ile Val Ser Met Gly Ala Trp Asn Ser Lys
        195                 200                 205

Leu Leu Ser Lys Leu Asn Leu Asp Ile Pro Leu Gln Pro Tyr Arg Gln
    210                 215                 220

Val Val Gly Phe Phe Asp Ser Asn Glu Ala Lys Tyr Ser Asn Asp Val
225                 230                 235                 240

Asp Tyr Pro Ala Phe Met Val Glu Val Pro Lys Gly Ile Tyr Tyr Gly
                245                 250                 255

Phe Pro Ser Phe Gly Gly Cys Gly Leu Lys Ile Gly Tyr His Thr Tyr
            260                 265                 270

Gly Gln Gln Ile Asp Pro Asp Thr Ile Asn Arg Glu Phe Gly Ala Tyr
        275                 280                 285

Gln Glu Asp Glu Ser Asn Leu Arg Asp Phe Leu Glu Lys Tyr Met Pro
    290                 295                 300
```

```
Glu Ala Asn Gly Glu Leu Lys Arg Gly Ala Ala Cys Met Tyr Thr Lys
305                 310                 315                 320

Thr Pro Asp Glu His Phe Val Ile Asp Thr His Pro Glu His Ser Asn
                325                 330                 335

Val Phe Val Ala Ala Gly Phe Ser Gly His Gly Phe Lys Phe Ser Ser
                340                 345                 350

Val Val Gly Glu Val Leu Ser Gln Leu Ala Thr Thr Gly Lys Thr Glu
            355                 360                 365

His Asp Ile Ser Ile Phe Ser Ile Asn Arg Pro Ala Leu Lys Gln Lys
        370                 375                 380

Thr Thr Ile
385

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gtaccggatc cgctagcttt ac                                           22

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
cgacggccag agatctacta g                                            21

<210> SEQ ID NO 5
<211> LENGTH: 1164
<212> TYPE: DNA
<213> ORGANISM: Bacillus sp. strain KS-11A
<220> FEATURE:
<221> NAME/KEY: CDS
<222> LOCATION: (1)..(1164)

<400> SEQUENCE: 5 atg agt aca cat ttt gat gtg att gtt gtt gga gca gga tca atg gga     48
Met Ser Thr His Phe Asp Val Ile Val Val Gly Ala Gly Ser Met Gly
1               5                   10                  15 atg gct gca ggg tac tat tta gca aaa caa gga gtc aaa aca tta ttg     96
Met Ala Ala Gly Tyr Tyr Leu Ala Lys Gln Gly Val Lys Thr Leu Leu
                20                  25                  30 gtg gat gca ttc gat ccg ccg cat aca gaa gga agc cat cac ggt gat    144
Val Asp Ala Phe Asp Pro Pro His Thr Glu Gly Ser His His Gly Asp
            35                  40                  45 act cgc att atc cgc cat gct tac ggt gaa gga aga gaa tat gtt cca    192
Thr Arg Ile Ile Arg His Ala Tyr Gly Glu Gly Arg Glu Tyr Val Pro
        50                  55                  60 ttt gca cta aga gca caa gaa tta tgg tat gaa ctt gaa aat gaa aca    240
Phe Ala Leu Arg Ala Gln Glu Leu Trp Tyr Glu Leu Glu Asn Glu Thr
65                  70                  75                  80 cac aat aag att ttt aca aaa aca ggc gtt cta gtt ttt ggt ccg aaa    288
His Asn Lys Ile Phe Thr Lys Thr Gly Val Leu Val Phe Gly Pro Lys
                85                  90                  95 ggt gaa tcc gat ttc gtt gcc gaa aca atg gag gca gct gca gaa cat    336
Gly Glu Ser Asp Phe Val Ala Glu Thr Met Glu Ala Ala Ala Glu His
```

```
Gly Glu Ser Asp Phe Val Ala Glu Thr Met Glu Ala Ala Glu His
            100                 105                 110 tca ttg act gtg gat tta ctt gag ggt gat gaa atc aat acg cgc tgg    384
Ser Leu Thr Val Asp Leu Leu Glu Gly Asp Glu Ile Asn Thr Arg Trp
        115                 120                 125 ccc ggc ata acg gtt cct gaa aac tat aat gca att ttt gaa cca aat    432
Pro Gly Ile Thr Val Pro Glu Asn Tyr Asn Ala Ile Phe Glu Pro Asn
    130                 135                 140 tca ggc gta ttg ttc agt gag aat tgt att cgt tca tac cgt gag ctg    480
Ser Gly Val Leu Phe Ser Glu Asn Cys Ile Arg Ser Tyr Arg Glu Leu
145                 150                 155                 160 gct gta gca aaa gga gca aaa att tta aca tat act cgt gtt gag gat    528
Ala Val Ala Lys Gly Ala Lys Ile Leu Thr Tyr Thr Arg Val Glu Asp
                165                 170                 175 ttt gaa gtt tct caa gac caa gtt aaa atc caa acg gca aat gga tcg    576
Phe Glu Val Ser Gln Asp Gln Val Lys Ile Gln Thr Ala Asn Gly Ser
            180                 185                 190 tac aca gct gat aaa tta atc gta agt atg ggt gct tgg aat agt aaa    624
Tyr Thr Ala Asp Lys Leu Ile Val Ser Met Gly Ala Trp Asn Ser Lys
        195                 200                 205 cta ctt tct aaa tta aat ctt gac atc cca tta cag cca tac cgc caa    672
Leu Leu Ser Lys Leu Asn Leu Asp Ile Pro Leu Gln Pro Tyr Arg Gln
210                 215                 220 gtt gta gga ttt ttt gat tct aat gaa gca aag tac agc aat gat gtg    720
Val Val Gly Phe Phe Asp Ser Asn Glu Ala Lys Tyr Ser Asn Asp Val
225                 230                 235                 240 gat tat cca gca ttc atg gta gaa gta cca aaa ggt att tat tac gga    768
Asp Tyr Pro Ala Phe Met Val Glu Val Pro Lys Gly Ile Tyr Tyr Gly
                245                 250                 255 ttc cca agc ttc ggt ggc tgc ggt ttg aaa ata ggg tat cat acg tat    816
Phe Pro Ser Phe Gly Gly Cys Gly Leu Lys Ile Gly Tyr His Thr Tyr
            260                 265                 270 ggt caa caa atc gac cct gat acg att aac cgt gaa ttt ggt gct tat    864
Gly Gln Gln Ile Asp Pro Asp Thr Ile Asn Arg Glu Phe Gly Ala Tyr
        275                 280                 285 caa gag gat gaa agt aat ctt cgc gat ttc ttg gaa aaa tat atg cca    912
Gln Glu Asp Glu Ser Asn Leu Arg Asp Phe Leu Glu Lys Tyr Met Pro
290                 295                 300 gaa gca aat ggc gag tta aaa cga ggc gca gtc tgt atg tac acg aaa    960
Glu Ala Asn Gly Glu Leu Lys Arg Gly Ala Val Cys Met Tyr Thr Lys
305                 310                 315                 320 aca cca gat gaa cat ttc gtg att gat act cat cca gaa cat tcc aat    1008
Thr Pro Asp Glu His Phe Val Ile Asp Thr His Pro Glu His Ser Asn
                325                 330                 335 gtt ttc gta gca gct ggt ttc tct gga cac ggc ttt aaa ttt tca agt    1056
Val Phe Val Ala Ala Gly Phe Ser Gly His Gly Phe Lys Phe Ser Ser
            340                 345                 350 gta gtc ggt gaa gtg tta agt caa tta gcg aca aca ggt aaa aca gaa    1104
Val Val Gly Glu Val Leu Ser Gln Leu Ala Thr Thr Gly Lys Thr Glu
        355                 360                 365 cat gat att tca att ttc tca ata aat cgt cct gct tta aaa cag aaa    1152
His Asp Ile Ser Ile Phe Ser Ile Asn Arg Pro Ala Leu Lys Gln Lys
370                 375                 380 aca acg att taa                                                    1164
Thr Thr Ile
385

<210> SEQ ID NO 6
<211> LENGTH: 387
<212> TYPE: PRT
```

<213> ORGANISM: Bacillus sp. strain KS-11A

<400> SEQUENCE: 6

```
Met Ser Thr His Phe Asp Val Ile Val Val Gly Ala Gly Ser Met Gly
1               5                   10                  15

Met Ala Ala Gly Tyr Tyr Leu Ala Lys Gln Gly Val Lys Thr Leu Leu
            20                  25                  30

Val Asp Ala Phe Asp Pro Pro His Thr Glu Gly Ser His His Gly Asp
        35                  40                  45

Thr Arg Ile Ile Arg His Ala Tyr Gly Glu Gly Arg Glu Tyr Val Pro
    50                  55                  60

Phe Ala Leu Arg Ala Gln Glu Leu Trp Tyr Glu Leu Glu Asn Glu Thr
65                  70                  75                  80

His Asn Lys Ile Phe Thr Lys Thr Gly Val Leu Val Phe Gly Pro Lys
                85                  90                  95

Gly Glu Ser Asp Phe Val Ala Glu Thr Met Glu Ala Ala Glu His
            100                 105                 110

Ser Leu Thr Val Asp Leu Leu Glu Gly Asp Glu Ile Asn Thr Arg Trp
        115                 120                 125

Pro Gly Ile Thr Val Pro Glu Asn Tyr Asn Ala Ile Phe Glu Pro Asn
    130                 135                 140

Ser Gly Val Leu Phe Ser Glu Asn Cys Ile Arg Ser Tyr Arg Glu Leu
145                 150                 155                 160

Ala Val Ala Lys Gly Ala Lys Ile Leu Thr Tyr Thr Arg Val Glu Asp
                165                 170                 175

Phe Glu Val Ser Gln Asp Gln Val Lys Ile Gln Thr Ala Asn Gly Ser
            180                 185                 190

Tyr Thr Ala Asp Lys Leu Ile Val Ser Met Gly Ala Trp Asn Ser Lys
        195                 200                 205

Leu Leu Ser Lys Leu Asn Leu Asp Ile Pro Leu Gln Pro Tyr Arg Gln
    210                 215                 220

Val Val Gly Phe Phe Asp Ser Asn Glu Ala Lys Tyr Ser Asn Asp Val
225                 230                 235                 240

Asp Tyr Pro Ala Phe Met Val Glu Val Pro Lys Gly Ile Tyr Tyr Gly
                245                 250                 255

Phe Pro Ser Phe Gly Gly Cys Gly Leu Lys Ile Gly Tyr His Thr Tyr
            260                 265                 270

Gly Gln Gln Ile Asp Pro Asp Thr Ile Asn Arg Glu Phe Gly Ala Tyr
        275                 280                 285

Gln Glu Asp Glu Ser Asn Leu Arg Asp Phe Leu Glu Lys Tyr Met Pro
    290                 295                 300

Glu Ala Asn Gly Glu Leu Lys Arg Gly Ala Val Cys Met Tyr Thr Lys
305                 310                 315                 320

Thr Pro Asp Glu His Phe Val Ile Asp Thr His Pro Glu His Ser Asn
                325                 330                 335

Val Phe Val Ala Ala Gly Phe Ser Gly His Gly Phe Lys Phe Ser Ser
            340                 345                 350

Val Val Gly Glu Val Leu Ser Gln Leu Ala Thr Thr Gly Lys Thr Glu
        355                 360                 365

His Asp Ile Ser Ile Phe Ser Ile Asn Arg Pro Ala Leu Lys Gln Lys
    370                 375                 380

Thr Thr Ile
385
```